United States Patent
Franzen

(10) Patent No.: US 7,193,223 B2
(45) Date of Patent: Mar. 20, 2007

(54) DESORPTION AND IONIZATION OF ANALYTE MOLECULES AT ATMOSPHERIC PRESSURE

(75) Inventor: Jochen Franzen, Bremen (DE)

(73) Assignee: Bruker Daltonik, GmbH, Bremen (DE)

( * ) Notice: Subject to any disclaimer, the term of this patent is extended or adjusted under 35 U.S.C. 154(b) by 75 days.

(21) Appl. No.: 11/003,017

(22) Filed: Dec. 2, 2004

(65) Prior Publication Data
US 2005/0199823 A1   Sep. 15, 2005

(30) Foreign Application Priority Data
Jan. 20, 2004   (DE) .................. 10 2004 002 729

(51) Int. Cl.
*H01J 27/00* (2006.01)
*H01J 49/10* (2006.01)

(52) U.S. Cl. ................ 250/425; 250/288; 250/282
(58) Field of Classification Search ............ 250/425
See application file for complete search history.

(56) References Cited

U.S. PATENT DOCUMENTS

| | | | |
|---|---|---|---|
| 4,861,988 A | | 8/1989 | Henion et al. |
| 5,294,797 A | * | 3/1994 | Frey et al. .............. 250/427 |
| 5,663,561 A | * | 9/1997 | Franzen et al. .............. 250/288 |
| 5,965,884 A | | 10/1999 | Laiko et al. |
| 2003/0071209 A1 | * | 4/2003 | Park et al. .................. 250/288 |
| 2003/0111600 A1 | | 6/2003 | Thomson et al. |
| 2004/0007673 A1 | * | 1/2004 | Coon et al. .................. 250/424 |
| 2004/0011953 A1 | * | 1/2004 | Chen et al. .................. 250/288 |
| 2005/0230635 A1 | * | 10/2005 | Takats et al. ................ 250/424 |

FOREIGN PATENT DOCUMENTS

| | | |
|---|---|---|
| DE | 199 11 801 C1 | 1/2001 |
| DE | 101 34 427 A1 | 2/2003 |
| EP | 0 860 858 B1 | 8/1998 |
| EP | 0964427 A2 | 12/1999 |
| WO | WO 02097857 A1 | 5/2002 |
| WO | WO 03/052399 A2 | 6/2003 |
| WO | WO 03/102537 A2 | 12/2003 |
| WO | WO 2004/030024 A2 | 4/2004 |
| WO | WO 2004/112074 A3 | 12/2004 |

* cited by examiner

*Primary Examiner*—Nikita Wells
*Assistant Examiner*—James J. Leybourne
(74) *Attorney, Agent, or Firm*—The Law Offices of Paul E. Kudirka

(57) ABSTRACT

The invention relates to the ionization of analyte molecules on a solid surface close to atmospheric pressure as an ion source for mass spectrometers. The invention uses a spray mist from an electrospray apparatus to ionize the analyte molecules, for example a spray mist created by spraying pure water, which generates predominantly multiply charged ions of the analyte molecules which are particularly suitable for fragmentation.

21 Claims, 2 Drawing Sheets

DESORPTION AND IONIZATION OF ANALYTE MOLECULES AT ATMOSPHERIC PRESSURE

FIELD OF THE INVENTION

The invention relates to the ionization of analyte molecules on a sample support close to atmospheric pressure as an ion source for mass spectrometers.

BACKGROUND OF THE INVENTION

The ionization of large biomolecules by matrix assisted laser desorption in high vacuum (Matrix Assisted Laser Desorption and Ionization=MALDI for short) for mass spectrometric analyses has been known since the end of the 80s. This type of analyte molecule desorption also works in gases at atmospheric pressure. DE 196 08 963 (Franzen 1995) describes how analyte molecules at atmospheric pressure can be favorably desorbed by the use of special matrix substances in order to be then introduced to a subsequent ionization with protonating ions. This produces an extremely high yield of analyte ions. The subsequent ionization is carried out using protonating ions generated by electron beams, for example beams of beta particles, corona discharges or UV lamps. The analyte ions are predominantly singly charged, as is the case with the original vacuum MALDI. As already happens with the well-known method of electrospray ionization, the ions generated are transferred into the vacuum of the mass spectrometer through a capillary.

In the two practically identical inventions U.S. Pat. No. 5,965,884 (V. V. Laiko and A. L. Burlingame) and EP 0 964 427 A2 (J. Bai, S. M. Fischer, and J. M. Flanagan) the MALDI method including the ionization of the analyte molecules as such, which is well-known from high vacuum, is carried out at atmospheric pressure. As is the case with vacuum MALDI, the analyte ions here are also predominantly singly charged.

The disclosure WO 02/097 857 A1 (C. M. Whitehouse) also suggests the generation of analyte ions by MALDI at atmospheric pressure but within a high-frequency ion guide system.

The current way of elucidating the sequence of biopolymers such as proteins is to subject the chain-shaped analyte ions to a suitable fragmentation process and to then use the daughter ion spectra thus generated to read the sequence of the amino acids of the chain. For this process it is advantageous if the chains are fragmented between each of the amino acids. Surprisingly, it has proven difficult to evenly fragment the singly charged ions generated during the MALDI process. This is especially true of MALDI ions generated at atmospheric pressure, which are immediately cooled in the ambient gas and hence have no excess intrinsic energy to bring into the fragmentation process. Soft fragmentation, such as occurs during multiple collision processes in ion traps, and also in multiple photon processes (IRMPD—Infrared Multiphoton Dissociation), is extremely unsuccessful here.

In contrast, doubly or higher charged analyte ions, such as those preferredly generated by electrospray ionization, are much easier to fragment between each amino acid even though they are also generated at atmospheric pressure. Collisional ion dissociation (CID) provides daughter ion spectra which can be used quite well to interpret the sequence. Daughter ion spectra fragmented from doubly charged biomolecules by electron capture dissociation (ECD) are even better for elucidating the structure and determining the sequence since, in this case, the daughter ion spectra generated are particularly easy to interpret.

For multiply charged negative ions, the EDD process can be used in a similar way to generate informative daughter ion spectra (EDD=electron detachment dissociation). This shoots an electron out of multiply charged negative ions and also leads to evenly distributed fragmentation.

SUMMARY OF THE INVENTION

The invention provides methods and devices for using the spray mist of an electrospray device to ionize analyte molecules which are desorbed from a sample support. Any desorption method like laser flashes, shock waves, thermal flash heating or charged droplet impact may be used to desorb the analyte molecules. The desorbed analyte molecules are protonized and hence ionized as a result of the large number of protons present either in the spray mist droplets or as free proton-water complexes vaporized from the mist droplets. The sheer surplus of protonating complexes in this case means that protonation can extend as far as the saturation limit of the analyte molecules for the acceptance of protons through their proton affinity or, also, depending on the charge strength of the spray mist, stop before this point. The spectra of the analyte substances obtained are similar to those obtained for analyte substances released by electrospray ionization.

The spray mist of an electrospray apparatus forms a spray mist cone which is generated, on the one hand, by the strong pull on the charged droplets to the drawing electrode and, on the other, by the Coulomb repulsion between the charged droplets. The Coulomb repulsion causes the droplets to move at right angles to the direction of spray, forming the cone. The droplets (and vaporized protons, mainly attached to water complexes) thus penetrate into the ambient gas. If pure water is sprayed, for example, many proton-water complexes are also to be found outside the visible spray mist cone; these complexes emerge from the spray mist cone as a result of the Coulomb repulsion and thus have a diffusion rate which is higher than that of the droplets, which are more strongly decelerated in the gas. The addition of methanol to water as spray fluid facilitates the spraying process and generates even more kinds of protonating complexes. In addition, the spray fluid is usually made sour by addition of low amounts of acids, e.g. trifluor acetic acid (TFA). If the ambient gas contains analyte molecules with a suitable proton affinity, these analyte molecules are ionized by protonation.

The electrospray process can be assisted in the normal way by a gas blown in coaxially to the spray capillary or at a sharp angle by nebulization, this jet of gas also entrains gas from the surroundings. If the gas from the surroundings contains desorbed analyte molecules, they are automatically introduced into the spray cone. The nebulizing gas used here usually is very clean, heated nitrogen.

Usually, a hot drying gas is allowed to counterflow towards the spray mist. The desorption of the analyte molecules can also be carried out into this drying gas which by itself moves into the spray mist.

The ion source with electrospray means and desorption means can also be used in particular for normal electrospray ionization. A combined operation, for example for the addition of mass calibration substance ions to the analyte ions, is also possible.

Multiple deprotonation using an excess of $OH^-$ ions from a negative spray mist can be used to generate multiply charged negative ions. The OH⁻ ions from correspondingly negatively charged water complexes each combine with one proton of the analyte molecule and leave the molecule as a neutral water molecule by deprotonating the analyte molecule; singly or multiply charged negative ions of the analyte substance remain behind.

BRIEF DESCRIPTION OF THE DRAWINGS

The above and further advantages of the invention may be better understood by referring to the following description in conjunction with the accompanying drawings in which.

DETAILED DESCRIPTION

Figure 1:
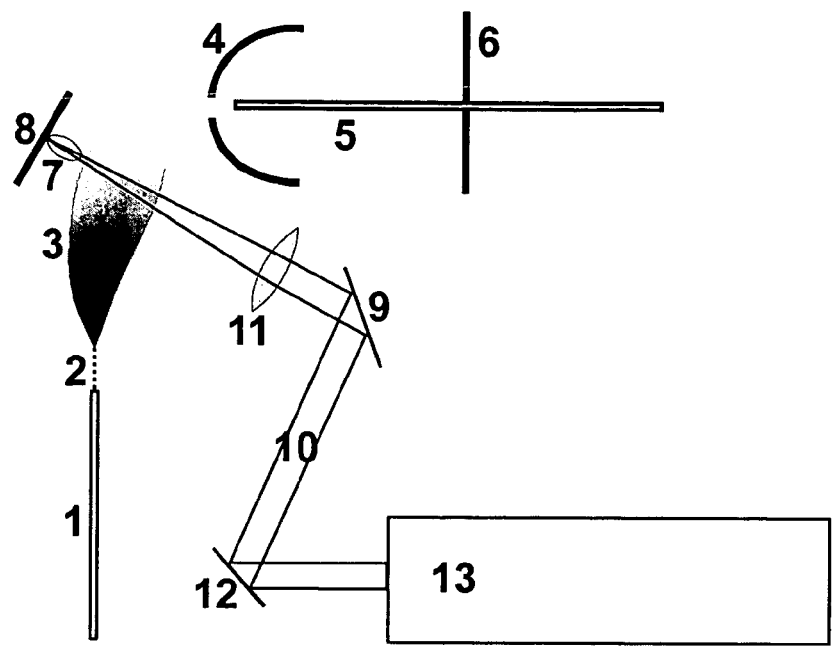
FIG. 1 is a schematic view of a first embodiment of the present invention.

A desorption of analyte molecules deposited on a sample support can be effected by application of pulses of energy. The desorption, for example, can be generated by a heating pulse applied to a strip of support material; more well-known, however, is the desorption by high-energy flashes of light, particularly flashes of laser light. Desorption is generated by the impingement of charged or neutral molecules. Other desorption methods are shock waves generated by laser light pulses to the backside of sample supports as described in U.S. Pat. No. 5,373,156, or impact by highly charged microdroplets ("Formation of multiply-charged ions from large molecules using massive-cluster impact", J. F. Mahoney et al., Rapid Comm. in Mass Spectrom. 1994, 8, 403–406). Desorption by means of flashes of light can be carr absorption of the sample support followed by a 'shaking off' of the analyte molecules, and also by the analyte molecules themselves taking up energy, in which case they run the risk of immediately decomposing, however.

A method of desorption which causes particularly little damage of the analyte molecules was found at the end of the 80s by Karas and Hillenkamp: matrix assisted laser desorption (MALDI). Here, the analyte molecules are diluted as much as possible and thus individually embedded in a matrix substance which is usually crystalline, but sometimes also liquid. The matrix substance here is chosen so that it can absorb the energy of the pulse of laser light, vaporizing explosively to a plume, in this case the analyte molecules also change into the free gaseous state. The separation of the analyte molecules from each other in the matrix substance means that the fraction of dimers and multimers of the analyte molecules in the desorption cloud is very small. The matrix substances are also chosen so that they are partly ionized in the plasma of the cloud and can ionize the analyte molecules by protonation.

This type of ionization by matrix assisted desorption by pulses of laser light was initially only applied in high vacuum, then in coarse vacuum, and later at atmospheric pressure. Since this ionization essentially only generates singly charged ions, only the desorbing part of the method, not the ionizing part, is of interest here.

Apart from the normal desorption of pure analyte molecules from a surface, especially laser desorption, which always includes a partial fragmentation of the analyte molecules, matrix assisted laser desorption is a method of desorption which causes very little damage to the substance and hence a desorption method preferred here for the subsequent ionization by an electrospray mist as defined by the invention.

Since this method of desorption does not have to take over the ionization as well, the matrix substance can be selected according to factors completely different to those for the well-known MALDI process. With respect to this invention, the job of the matrix substance is restricted to the absorption of the laser light energy and the vaporization of the analyte molecules without causing damage. Preferably, the matrix substance should also be suitable for the acceptance of analyte substances, whether by the formation of a solid solution or by surface adsorption. As already embodied in DE 196 08 963, it is particularly favorable to select a matrix substance which decomposes into small molecular components in the flash of laser light, these components being in a gaseous state in the desorption cloud. One example of this is cellulose dinitrate (frequently termed dinitrocellulose) which decomposes in water, carbon dioxide and nitrogen. Such explosives do not deliver any ions forming chemical noise.

After this laser desorption process, the desorption cloud containing analyte molecules in a gaseous state shall now interact with the spray mist of the electrospray apparatus.

Figure 2:
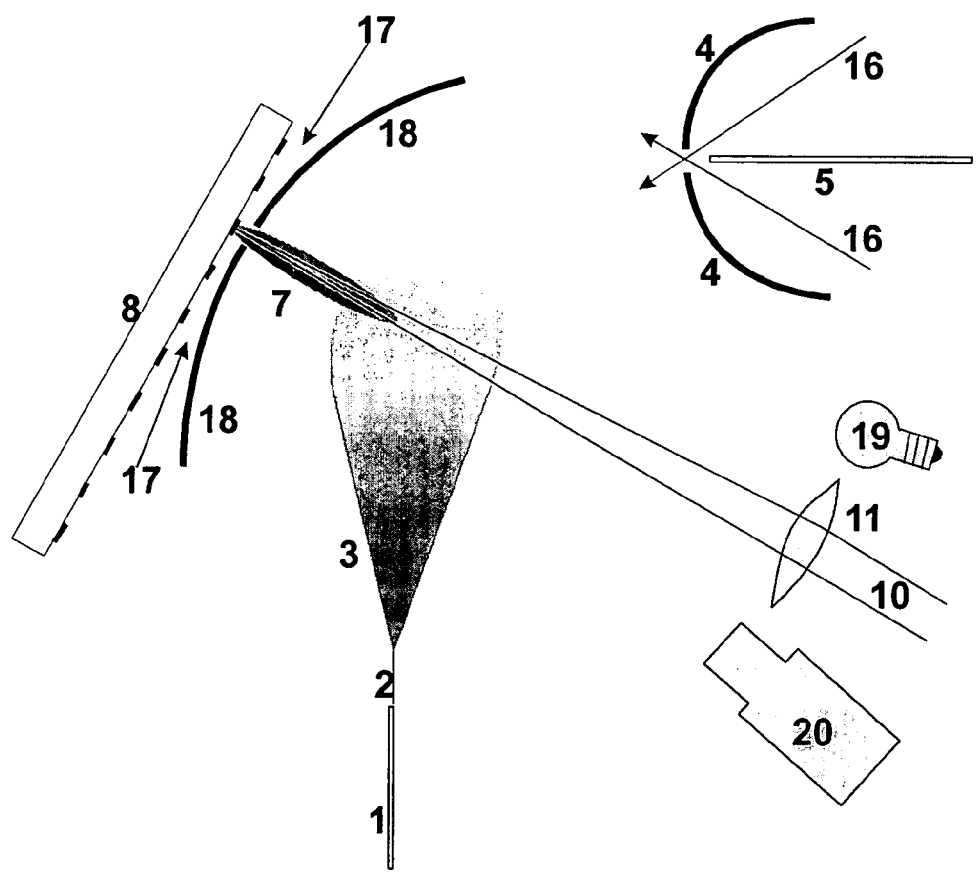
FIG. 2 is a schematic view of an embodiment similar to that of FIG. 1, in which a further electrode is located in front of the sample support.
Figure 3:
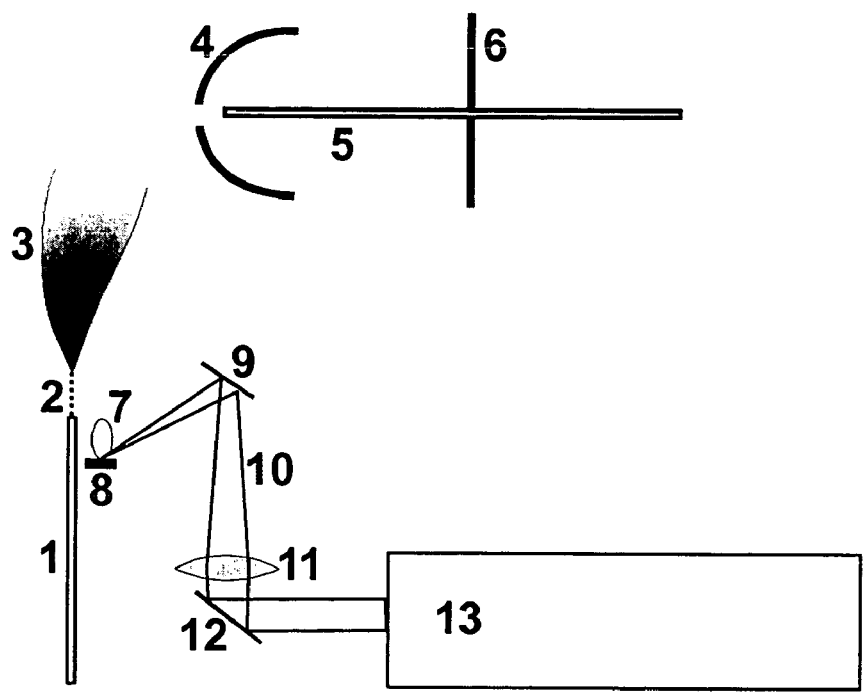
FIG. 3 is a schematic view of an embodiment in which a sample support is positioned next to the spray capillary so that the desorption cloud can rise into the spray mist.

Several arrangements of sample supports loaded with analyte molecules and matrix substance in different positions with respect to the spray capillary are shown in FIGS. 1 to 3.

As shown in FIG. 1, an electrospray apparatus comprises a capillary 1, in which the spray fluid is introduced, and a counterelectrode 4, which is used to apply a high voltage of a few kilovolts to build up an electric field between counterelectrode 4 and the tip of capillary 1, this electric field has a particularly high field strength around the tip of capillary 1. The capillary tip can be a standard capillary end, or it can be especially pointed. The spray fluid usually contains a certain amount of easily polarizable water. The surface of the spray fluid is polarized by the electric field on the capillary tip and the force of the field forms it into a so-called Taylor cone and, if the voltages and separations are correctly adjusted, a jet of fluid 2 is drawn from this tip which dissolves immediately, or after a short flight time, into minute, highly charged droplets which form the spray mist 3. The droplets vaporize by losses of fluid molecules and protons (or $OH^-$ ions in the case of negative spraying). To achieve the desired vaporization of the droplets it is favorable to blow a stream of hot drying gas 16 (as shown in FIG. 2) at temperatures between 80° and 300° Celsius towards the spray mist 3. As preferred drying gas, usually pure nitrogen is chosen.

It is by no means the case that only pure protons are formed when the droplets vaporize, on the contrary, the protons in the ambient gas are predominantly bonded to water complexes of the form $(H_2O)_nH^+$. These water complexes, for example $H_5O_2^+$ or $H_7O_3^+$, can ionize particularly well by proton donation, the proton affinity energy released being largely absorbed by the water complex. Ionization processes such as this, which do not damage the substance ("soft ionization processes"), have been known for a long time as "chemical ionization".

It is also possible to add a substance to the spray fluid which is initially ionized and which is particularly suitable for a protonating ionization of the analyte molecules. Examples are alcohols, ketones or organic acids, which favorably should have molecular masses in the range of around 70 to 130 atomic mass units.

The spraying can be assisted by a jet of spray gas introduced coaxially, as happens with a nebulizer, in order to generate particularly fine droplets. This jet of nebulized gas, preferably clean nitrogen, can also be heated in a similar way to the drying gas.

Referring again to FIG. 1, a metal sample support 8 for the analyte substances is positioned directly next to the spray mist 3, at an electrical potential between that of the counterelectrode 4 and the capillary tip 1 but closer to the potential of counterelectrode 4. The electrospray ionization of pure water (or pure water/methanol mixture) is effected by the high voltage of a few kilovolts between the combined potential of the counterelectrode 4 and the sample support 8, on the one hand, and the potential of the capillary tip 1 on the other. A fine jet of spray 2 is created which fans out into a spray mist 3. The jet of spray microdroplets can by itself be used to desorb the analyte molecules, but a better localization of the desorption point is achieved by a focused laser pulse. A pulse of laser light from the pulsed laser 13 is focused onto the sample support via mirrors 9 and 12 and lens 11, and generates the desorption cloud 7 out of the sample with matrix and analyte material applied to the surface of the sample support 8. The analyte molecules of the desorption cloud 7 are ionized by the charged droplets and the proton-water complexes of the spray mist cloud 3. Under the influence of the potential difference between sample plate 8 and the counterelectrode 4 they then migrate to counterelectrode 4. Here, the potential at the inlet capillary 5 reaches through the aperture of the counterelectrode 4 and draws the ions to the opening of the inlet capillary 5. Here they are sucked through the inflowing ambient gas, preferably nitrogen, through the wall 6, which is only outlined here, into the vacuum system of the mass spectrometer.

In FIG. 2, an electrode 18 is also introduced in front of the sample support in order to be able to introduce the desorption cloud 7 to the spray mist 3 by means of a supplementary stream 17 of pure nitrogen. The electrode 18 also serves to shape the electric field, to effect the electrospray ionization and to guide the ions to the inlet capillary 5 behind the counterelectrode 4. Thanks to their ion mobility, the ions migrate exactly along the electric field lines, being only marginally influenced by the relatively slow gas streams. In this FIG. 2, a video camera 20 with illuminating lamp 19 is also introduced in order to be able to monitor the position of the sample on the sample support 8. The sample support 8 can be moved in two directions parallel to its surface in order to be able to introduce the samples to the focus of the beam of laser light 10.

FIG. 3 schematically shows an array in which the sample support 8 is arranged adjacent to the spray capillary 1 so that the desorption cloud 7 can rise into the spray mist 3. Vertical spraying allows the desorption cloud 7 to migrate upwards by virtue of its thermal uplift and enter the spray mist cone 3. As an alternative to the uplift (or in addition to it), an artificially generated gas stream, similar to the gas stream 17 in FIG. 2, can also transport the desorption cloud 7 to the spray mist 3. By using a nebulizing spray gas, which is usually blown in through a sheath capillary (not shown in the illustrations) coaxial to the spray capillary, it is possible to suck the analyte molecules together with their ambient gas into the gas stream and to introduce them to the spray mist.

Figure 4:
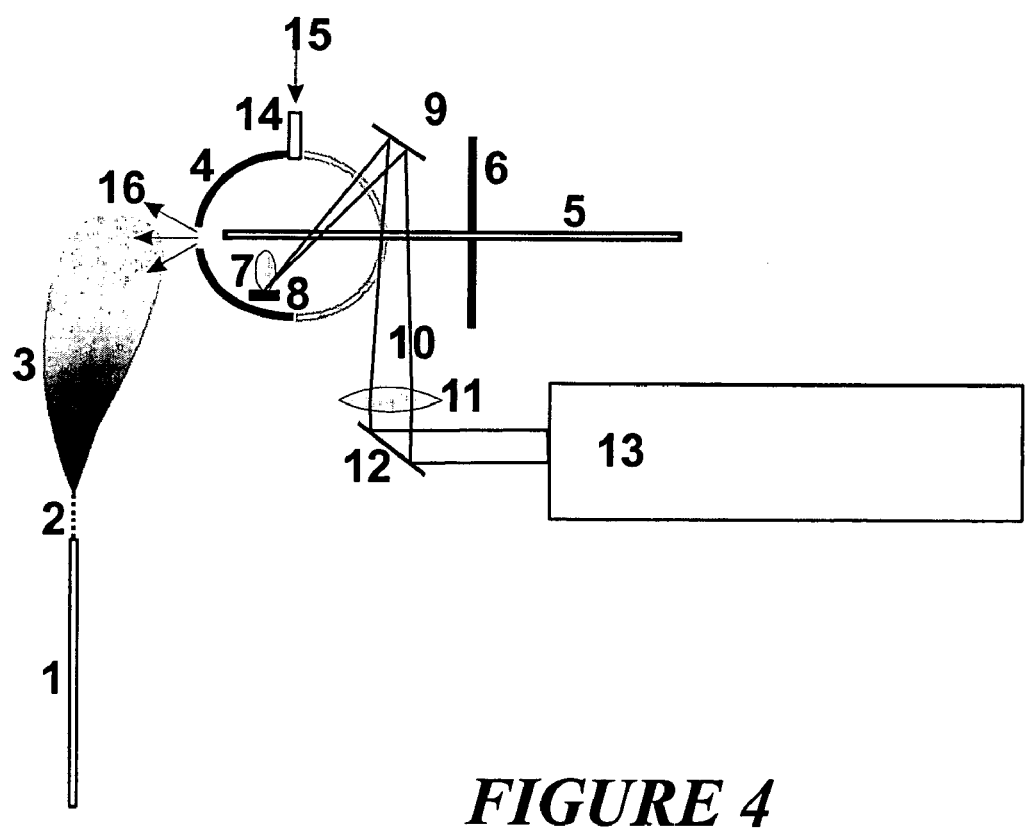
FIG. 4 is a schematic view of an embodiment in which the analyte molecules from a sample support are desorbed into a hot drying gas that is introduced to the spray mist.

A further arrangement desorbs the analyte molecules into the hot drying gas which is blown towards the spray cone 3 as a stream of hot gas 16, as represented schematically in FIG. 4. In FIG. 4, the same numbers are used for the labeling as are used in FIGS. 1 to 3; the only difference is the pipe 14 for blowing a heated drying gas 15 into the space surrounding the inlet capillary 5. The drying gas emerges from the aperture in the counterelectrode 4 as a stream of hot gas 16 and is thus blown towards the spray mist 3. This arrangement is well suited to use pulsed laser diodes as light sources.

The devices can be operated at atmospheric pressure, and also at pressures close to atmospheric pressure in the pressure range between 100 and 1200 hectopascal if this is expedient to produce streams of gas, or for other reasons.

This method of ionizing desorbed analyte molecules makes it possible to generate predominantly multiply charged analyte ions. In the molecular mass range between 1000 and 5000 atomic mass units, the doubly charged ions are most frequent in this case. These ions can be fragmented using the usual means in tandem mass spectrometers; the fragments then can be used to acquire daughter ion mass spectra which provide information for the sequence determination.

A device for the ionization of desorbed analyte molecules according to this invention thus contains a sample support carrying analyte molecules, and means for electrospray ionization with spray capillary, counterelectrode and voltage supply. The device may further contain a desorption device, preferably a pulse laser or a pulsed laser diode, for the desorption of the analyte ions. The sample support is arranged in such a way that the desorbed molecules reach the spray mist cone either on their own or with the help of gas streams. Examples for such devices are shown schematically in FIGS. 1 to 4.

For mass spectrometric analysis, a device for removing the ionized analyte molecules by suction with electrode 4 and the inlet capillary 5 is present, which introduces the analyte ions to the mass spectrometer in order to acquire a mass spectrum and especially also daughter ion spectra.

In order to monitor the desorption process, the sample can be observed using a video camera 20 with illumination apparatus 19. It can thus be optimally introduced to the focus of the pulse of laser light with the help of the movement device for the sample support 8.

The device for electrospray ionization can moreover be equipped with a nebulizing gas feeder and/or with a hot drying gas feeder, here the desorption may take place into the nebulizing gas or into the drying gas.

To introduce the spray fluid to the spray capillary, a special apparatus, for example a syringe pump, can be present. A double syringe pump with supply container for automatic refilling can ensure prolonged operation in such a case.

The apparatus for electrospray ionization can also be used independently of the desorption of analyte molecules by adding the analyte molecules to the spray fluid in dissolved form. It is then possible to couple mass spectrometric analysis with chromatographic or electrophoretic separation methods. The invention thus presents a combination ion source which can easily be switched from desorption mode to a purely electrospray ionization mode and back again. All that is needed is to change the supply of the spray capillary from the separation unit to the double syringe pump. It is also possible to set a mode which ionizes both desorbed substances as well as substances introduced via the spray fluid. In this way it is possible to introduce special substances for an internal mass calibration, for example.

If the direction of spray is vertically upwards, and the sample desorbs not too far below the spray mist 3, then the uplift of the desorption cloud 7 in the ambient gas along the spray capillary makes it easy for it to reach the region near the spray mist 3. The uplift can also be assisted or even substituted by a specially generated stream of gas.

The particular advantages of this type of ionization of samples desorbed from solid form, besides delivering doubly and triply charged analyte ions for favorable fragmentation, lie in the fact that the analyte molecules do not have to be introduced in liquid form, as is the case with pure electrospray ionization. The introduction in liquid form is always slow. While introduction in liquid form makes it possible to create a direct coupling with chromatographic or electrophoretic separation methods, the analysis is always bound to the time window of the chromatographic or electrophoretic peaks. When using solid sample preparations on solid sample supports, the situation is completely different. On the one hand, the samples can be analyzed one immediately after the other with no time delay, on the other, for the analysis of a sample which, if necessary, requires the switching over to daughter ion mode, all the time that is required can be taken. The sliding of the sample support from one sample location to the other occurs in fractions of a second. This enables a level of sample throughput to be achieved which is not possible by coupling with separation methods.

There are many more advantages of a desorption from a sample support such as a resolved analysis of organic material or the analysis of native (undigested) proteins, which often elude a chromatographic separation, but these advantages, which are well-known to the specialist, will not be gone into individually here.

The sensitivity of the method is here no less than that of pure electrospray ionization since, in both cases, practically all analyte molecules are ionized. Ion losses do occur, however, just as they do with electrospray ionization, when ions are introduced into the vacuum system of the mass spectrometer and when ions are separated off from the gas which also flows in the vacuum.

All types of solid bodies can be used as sample supports. In contrast to MALDI in time-of-flight spectrometers, they do not have to be conductive or particularly level. Thin tapes, as are used in cassette recorders, can be used. Advantageous are also sample supports in the shape of microtitre plates, since they can easily be filled in commercially available pipetting robots. Special embodiments allow an automatic interchange of sample supports here, for example by means of commercially available plate introduction robots.

What is claimed is:

1. Method for the ionization of analyte molecules close to atmospheric pressure, comprising the steps
   (a) providing analyte molecules on a sample support,
   (b) desorbing the analyte molecules, and
   (c) ionizing the analyte molecules by the spray mist generated from a spray fluid with an electrospray apparatus.

2. Method according to claim 1 wherein a clean solvent or solvent mixture is sprayed in the electrospray apparatus.

3. Method according to claim 1 wherein substances which assist the ionization of the desorbed analyte molecules are added to the spray fluid of the electrospray apparatus.

4. Method according to claim 1 wherein substances which form an internal mass reference for the evaluation of the mass spectra are added to the spray fluid of the electrospray apparatus.

5. Method according to claim 1 wherein essentially water or water/alcohol mixtures are sprayed in the electrospray apparatus.

6. Method according to claim 1 wherein the electrospraying in the electrospray apparatus is assisted by a nebulizing spray gas blown in coaxially to the spray capillary of the electrospray apparatus.

7. Method according to claim 6 wherein the nebulizing gas transports the desorbed analyte molecules into the spray mist.

8. Method according to claim 1 wherein the analyte molecules are desorbed from the sample support by the spray mist.

9. Method according to claim 1 wherein the analyte molecules are desorbed from the sample support by a pulse of light.

10. Method according to claim 9 wherein the analyte molecules are desorbed from the sample support by a pulse of laser light.

11. Method according to claim 9 wherein the desorption of the analyte molecules is assisted by a solid or liquid matrix substance, with the matrix substance containing the analyte molecules in solid or liquid solution or adsorbed on the surface.

12. Method according to claim 11 wherein the matrix substance is at least partially decomposed by the pulse of light.

13. Method according to claim 1 wherein the analyte molecules are desorbed from the sample support by rapid heating of the sample support.

14. Method according to claim 1 wherein the sample support is located in the vicinity of the electrode of the electrospray apparatus generating the electric field for spraying, the potential difference between this electrode and the sample support being either small or non-existent.

15. Method according to claim 1 wherein the sample support is located next to a spray capillary of the electrospray apparatus, somewhat set back from the tip of the capillary, the potential difference between the spray capillary and the sample support being either small or non-existent.

16. Method according to claim 1 wherein the sample support is located in a supply of the hot drying gas.

17. Device for the ionization of analyte molecules close to atmospheric pressure, comprising
    (a) a sample support for the analyte molecules,
    (b) an electrospray apparatus for electrospraying fluids, generating an electrospray mist, and
    (c) a desorbing apparatus for desorbing the analyte molecules from the sample support.

18. Device according to claim 17 wherein the device is also suitable for the electrospray ionization of analyte molecules dissolved in the spray fluid.

19. Device according to claim 17 further comprising a video camera and an illumination apparatus for observing locations where analyte molecules are present on the sample carrier plate.

20. Device according to claim 17 further comprising a movement device for sliding the sample support parallel to its surface in two directions.

21. Device according to claim 17 wherein the electrospray mist desorbs the analyte molecules.

* * * * *